(12) United States Patent
Miyamoto et al.

(10) Patent No.: US 12,017,088 B2
(45) Date of Patent: Jun. 25, 2024

(54) RADIOTHERAPY DEVICE AND RADIOTHERAPY METHOD

(71) Applicant: National University Corporation Hokkaido University, Sapporo (JP)

(72) Inventors: Naoki Miyamoto, Sapporo (JP); Kikuo Umegaki, Sapporo (JP); Shinichi Shimizu, Sapporo (JP); Satoshi Tomioka, Sapporo (JP); Seishin Takao, Sapporo (JP)

(73) Assignee: National University Corporation Hokkaido University, Sapporo (JP)

( * ) Notice: Subject to any disclaimer, the term of this patent is extended or adjusted under 35 U.S.C. 154(b) by 732 days.

(21) Appl. No.: 17/258,736

(22) PCT Filed: May 23, 2019

(86) PCT No.: PCT/JP2019/020395
§ 371 (c)(1),
(2) Date: May 25, 2021

(87) PCT Pub. No.: WO2020/012785
PCT Pub. Date: Jan. 16, 2020

(65) Prior Publication Data
US 2021/0268312 A1 Sep. 2, 2021

(30) Foreign Application Priority Data

Jul. 9, 2018 (JP) .................................. 2018-129750

(51) Int. Cl.
*A61N 5/10* (2006.01)
*A61B 6/00* (2006.01)
*A61B 6/03* (2006.01)

(52) U.S. Cl.
CPC ........... *A61N 5/103* (2013.01); *A61N 5/1049* (2013.01); *A61B 6/032* (2013.01); *A61B 6/5247* (2013.01);
(Continued)

(58) Field of Classification Search
CPC ................. A61N 5/103; A61N 5/1049; A61N 2005/1051; A61N 2005/1061;
(Continued)

(56) References Cited

U.S. PATENT DOCUMENTS 6,307,914 B1 10/2001 Kunieda
2006/0074292 A1 4/2006 Thomson
(Continued)

FOREIGN PATENT DOCUMENTS

JP 2000-167072 A 6/2000
JP 2008-514352 A 5/2008
(Continued)

OTHER PUBLICATIONS

International Search Report for Application No. PCT/JP2019/020395, mailed Jul. 16, 2019, with English translation (5 pages).
(Continued)

*Primary Examiner* — David P Porta
*Assistant Examiner* — Mamadou Faye
(74) *Attorney, Agent, or Firm* — Nixon Peabody LLP

(57) ABSTRACT

This radiotherapy device comprises: an X-ray irradiation device and an X-ray camera for detecting the position of a specific landmark present in an irradiation target; a storage unit which, with one from among a plurality of time-lapse three-dimensional CT images including the landmark and obtained beforehand during treatment planning used as a reference images, stores the relationship between the displacement of the landmark position from that in the reference image to that in another three-dimensional CT image,
(Continued)

CT IMAGE IN CORONAL DIRECTION SHOWING CORRELATION WITH BRIGHTNESS and the deformation of each of the sites in the other CT image, obtained by analysis thereof; and an image processing unit, a deformation amount evaluation unit, and a display unit, that estimate the deformation of each of the sites and reproduce the estimated three-dimensional CT image, according to the position of the landmark detected and the relationship stored by the storage unit.

7 Claims, 9 Drawing Sheets

(52) U.S. Cl.
CPC ....... *A61B 6/541* (2013.01); *A61N 2005/1051* (2013.01)

(58) Field of Classification Search
CPC .... A61N 5/1067; A61B 6/032; A61B 6/5247; A61B 6/541; A61B 6/03
See application file for complete search history.

(56) References Cited

U.S. PATENT DOCUMENTS

| | | |
|---|---|---|
| 2014/0226884 A1 | 8/2014 | Porikli |
| 2014/0241497 A1 | 8/2014 | Keall |
| 2016/0143576 A1 | 5/2016 | Symon |
| 2016/0217560 A1 | 7/2016 | Tahmasebi Maraghoosh |
| 2017/0043184 A1 | 2/2017 | Mori |
| 2020/0320722 A1* | 10/2020 | Jordan ................. A61N 5/10 |

FOREIGN PATENT DOCUMENTS

| | | |
|---|---|---|
| JP | 2015-535434 A | 12/2015 |
| JP | 2016-536035 A | 11/2016 |
| WO | WO 2015/125600 A1 | 8/2015 |

OTHER PUBLICATIONS

Written Opinion of International Searching Authority for Application No. PCT/JP2019/020395, mailed Jul. 16, 2019, with English translation (9 pages).
A. Fassi et al.; "Tumor Tracking Method Based on a Deformable 4D CT Breathing Motion Model Driven by an External Surface Surrogate"; Int. J. Radiation Oncol. Biol. Phys., vol. 88, No. 1, pp. 182-188; 2014 (7 pages).

* cited by examiner

CT IMAGE IN CORONAL DIRECTION SHOWING CORRELATION WITH BRIGHTNESS

CT IMAGE IN SAGITTAL DIRECTION SHOWING CORRELATION WITH BRIGHTNESS

CT IMAGE IN CORONAL DIRECTION IN EXHALATION PHASE

CT IMAGE IN CORONAL DIRECTION IN INSPIRATION PHASE

SYNTHESIZED IMAGE IN CORONAL DIRECTION IN INSPIRATION PHASE DETERMINED THROUGH CALCULATION

IMAGE SHOWING DIFFERENCE OF CT IMAGES

RADIOTHERAPY DEVICE AND RADIOTHERAPY METHOD

CROSS-REFERENCE TO RELATED APPLICATION

This application is a U.S. National Stage of International Application No. PCT/JP2019/020395, filed May 23, 2019, which is related to and claims the benefit and priority of Japanese Patent Application No. 2018-129750, filed Jul. 9, 2018, the contents of which are incorporated herein in their entireties by reference.

TECHNICAL FIELD

The present disclosure relates to a radiotherapy apparatus and a radiotherapy method.

BACKGROUND

In the related art, in radiotherapy, radiation is irradiated onto a diseased part, such as a cancer tumor, which moves with respiration or the like of a patient while minimizing exposure of normal sites to the radiation. For this purpose, real-time tumor-tracking radiotherapy is performed in which a marker which is placed near the diseased part in a body is monitored in real time, and the radiation is irradiated only when a three-dimensional position of the marker is present in a planned region (refer to Patent Document 1).

In addition, in radiotherapy with respect to cancer in a liver, a lung, or the like, in order to accurately irradiate the radiation onto the diseased part which moves with the respiration, a method is proposed in which a motion of a surface of an abdominal wall is monitored and the radiation is irradiated at a particular respiration phase (for example, an exhalation phase or an inspiration phase) (refer to Patent Document 2).

CITATION LIST

Patent Literature

Patent Document 1: JP 2000-167072 A
Patent Document 2: JP 2008-514352 A

SUMMARY

Technical Problem

The only parameter monitored in the real-time tumor-tracking radiotherapy of Patent Document 1 is the three-dimensional position of the marker, and the structures of the diseased part itself or of peripheral organs are not taken into consideration. Further, in Patent Document 2, only the exhalation/inspiration phases or representative point positions of the cancer are referred to, and three-dimensional deformation or the like of organs around the cancer is not taken into consideration. In reality, a positional relationship between the marker and the diseased part changes during therapy, as does the structure of the peripheral organs. Therefore, detection of states of the peripheral organs is desired, in order to achieve more precise irradiation to the diseased part (irradiation target position).

In addition, because the respiration motion within the body changes day by day, for example, there are cases in which the position of the tumor during the exhalation differs from that during CT imaging at the time of therapy planning. In such cases, it may be difficult to quickly judge whether or not the therapy should be continued. Currently, measures are taken; for example, the therapy is not performed until the respiration motion is settled or the CT image is again captured, but these measures result in an increase in the therapy time. Thus, obtaining the CT image in a short amount of time according to the current state is desired.

Further, in particle beam therapy, a range of the particle beam significantly varies depending on a status of the peripheral organs. Therefore, there may be cases in which an expected therapy cannot be performed unless the position of the diseased part which is the irradiation target is the same between the time of therapy planning and the time of the therapy, and the statuses of the peripheral organs are also the same between these times. Thus, if it becomes possible to evaluate in real time not only the position of the cancer, but also the three-dimensional structure including the peripheral organs, accuracy can be improved by performing the therapy in a state extremely close to the state at the time of the therapy planning.

Solution to Problem

According to one aspect of the present disclosure, there is provided a radiotherapy apparatus comprising: a detector unit that detects a landmark present in an irradiation target; a storage unit that stores a relationship between a displacement from a position of the landmark in a reference image, which is one three-dimensional CT image among a plurality of three-dimensional CT images of the irradiation target including the landmark, taken with elapse of time, and which are obtained in advance during therapy planning, to a position of the landmark in another three-dimensional CT image, and deformation of each site in the other CT image; and a three-dimensional CT image reproducing unit that estimates deformation of each site by referring to the relationship and according to the position of the landmark detected by the detector unit during therapy in which a therapeutic radiation is irradiated onto the irradiation target, and that reproduces an estimated three-dimensional CT image.

According to another aspect of the present disclosure, the radiotherapy apparatus may further comprise a control unit that controls irradiation of the therapeutic radiation based on the reproduced three-dimensional CT image.

According to another aspect of the present disclosure, the control unit may compare the reproduced three-dimensional CT image and a three-dimensional CT image which is obtained in advance during therapy planning, and may suspend the irradiation of the therapeutic radiation when a difference between the three-dimensional CT images is greater than or equal to a predetermined level.

According to another aspect of the present disclosure, the landmark may include a metal marker, and the detector unit may include an X-ray camera which detects the metal marker.

According to another aspect of the present disclosure, the landmark may include a surface position of the irradiation target, and the detector unit may include a surface position detector unit which detects the surface position.

According to another aspect of the present disclosure, there is provided a radiotherapy method in which therapeutic radiation is irradiated onto an irradiation target, the method comprising: during therapy planning, producing a plurality of three-dimensional CT images of the irradiation target including a landmark present in the irradiation target, taken with elapse of time, analyzing a relationship between a displacement from a position of the landmark in a reference image, which is one three-dimensional CT image among the plurality of three-dimensional CT images which are obtained, to a position of the landmark in another three-dimensional CT image, and deformation of each site in the other CT image, and storing the relationship which is obtained; and, during therapy in which a radiation is irradiated onto the irradiation target, detecting the position of the landmark, estimating deformation of each site by referring to the relationship and according to the detected position of the landmark, and obtaining a three-dimensional CT image.

According to another aspect of the present disclosure, the irradiation of the therapeutic radiation may be controlled based on the three-dimensional CT image which is obtained.

Advantageous Effects

According to the present disclosure, a three-dimensional CT image obtained by detecting a landmark may be obtained, and appropriate control of the irradiation of therapeutic radiation may be applied using the obtained three-dimensional CT image.

DESCRIPTION OF EMBODIMENTS

An embodiment of the present disclosure will now be described with reference to the drawings. The present disclosure is not limited to the embodiment described herein.
[Overall Structure of Apparatus]

Figure 1:
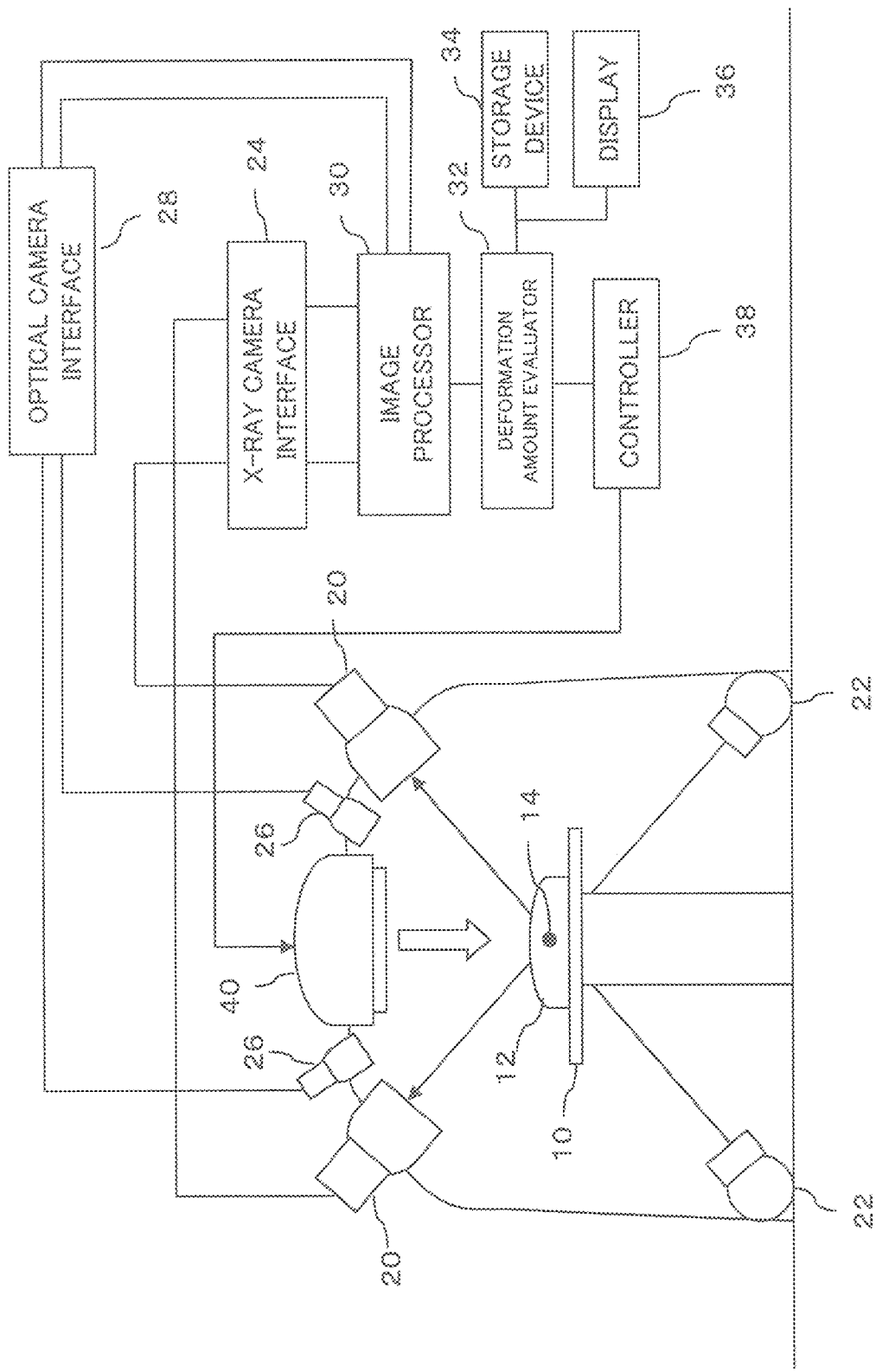
FIG. 1 is a diagram showing a structure of a radiotherapy apparatus according to an embodiment of the present disclosure.

FIG. 1 is a diagram showing an overall structure of a radiotherapy apparatus according to an embodiment of the present disclosure.

In a body of a patient 12 who is secured on a therapeutic table 10, a marker made of a metal (metal marker) 14 is embedded as a landmark. The marker 14 is, for example, a metal ball with a diameter of about 1 to 2 mm, and is embedded in advance at a position near a diseased part.

Two X-ray cameras 20, 20 are provided around the therapeutic table 10. At positions opposing the two X-ray cameras 20, 20 with the patient 12 therebetween, two X-ray irradiation apparatuses 22, 22 are placed.

X-ray beams from the X-ray irradiation apparatuses 22, 22 pass through predetermined sites of the patient 12 on the therapeutic table 10, and are incident on the opposing X-ray cameras 20, 20. The X-ray cameras 20, 20 output electrical signals for see-through images of the patient (irradiation target) 12, based on the incident X-rays.

Image signals from the two X-ray cameras 20, 20 are input to an image processor 30 through an X-ray camera interface 24. The X-ray cameras 20, 20 and the X-ray irradiation apparatuses 22, 22 form a detector unit of the landmark.

Further, two optical cameras 26, 26 are placed above the therapeutic table 10. An image of a body surface of the patient 12 (surface of the irradiation target) is captured by these optical cameras 26, 26, and the obtained image signals are input to the image processor 30 through an optical camera interface 28.

The image processor 30 applies an image process to the image signals from the two X-ray cameras 20, 20, to identify the marker 14 embedded in the body of the patient 12. Then, a three-dimensional position of the identified marker 14 is specified. That is, two-dimensional coordinates of the marker 14 in the images obtained by the two X-ray cameras 20, 20 are specified, and a three-dimensional position of the marker 14 is detected based on the positions of the two X-ray cameras 20, 20, which are known in advance, and the coordinates of the marker 14 in the two obtained images.

The two optical cameras 26, 26 are provided as a surface detection apparatus. A three-dimensional position of the body surface (surface position) is detected based on the images of the body surface obtained by the two optical cameras 26, 26, and positions of the optical cameras 26, 26. That is, a three-dimensional position of the body surface is detected based on the obtained body surface images and the positions of the optical cameras 26, 26. The three-dimensional position of the body surface may be set as the landmark position in place of the marker position, or, alternatively, both positions may be used as the landmark position.

The marker position and the body surface position obtained by the image processor 30 are supplied to a deformation amount evaluator 32. A storage device (storage unit) 34 is connected to the deformation amount evaluator 32, and stores the CT three-dimensional image obtained during therapy planning, and also a relationship of deformation of peripheral tissues, corresponding to an amount of change of the marker position or an amount of deformation of the body surface. The relationship will be described later in detail. For the body surface position, the data of the three-dimensional position of the body surface as a whole may be used, or, alternatively, statistical data such as an average and a standard deviation may be used. Further alternatively, the positions may be divided into a plurality of areas, and the statistical data for each of the divided areas may be used.

The deformation amount evaluator 32 successively calculates estimated three-dimensional CT images based on the marker position and the body surface position which are successively input, and the relationship stored in the storage device 34. The obtained CT image is displayed on a display 36 in real time.

The obtained three-dimensional CT image is also supplied to a controller (control unit) 38. The controller 38 specifies a position of the diseased part based on the three-dimensional CT image, and controls a beam irradiation apparatus 40 such as a linac, for irradiating a therapeutic radiation beam onto the patient 12. For example, the diseased part may be specified by applying an image process, such as pattern matching, to the three-dimensional CT image data. Desirably, the three-dimensional CT image data are formed as voxel data.

For the beam irradiation apparatus 40, an irradiation position of the therapeutic radiation beam from the irradiation apparatus 40 may be defined in advance, and the therapeutic radiation beam may be irradiated when the position of the diseased part (cancer) matches the irradiation position, which is determined based on the three-dimensional CT image. Alternatively, the beam irradiation apparatus 40 may be an apparatus which irradiates while rotating. In this case, there may be performed volumetric modulated arc therapy which takes into consideration deformation of the peripheral tissues. Further, the radiation position of the therapeutic radiation may be controlled to trace a detected target position.

Further, a difference is calculated by comparing the obtained three-dimensional CT image and the CT image which is used during the therapy planning. When the obtained difference is greater than a threshold which is defined in advance, it may be judged that the planned therapy cannot be performed, and the irradiation of the therapeutic radiation may be suspended.

In a particle beam therapy which uses a heavy particle beam, a proton beam, or the like, influence of a thickness (water-equivalent thickness) of the therapeutic radiation beam path is great. Therefore, the water-equivalent thickness in the therapeutic radiation beam path may be evaluated based on the obtained three-dimensional CT image, and an intensity or the like of the therapeutic radiation beam may be controlled based on a difference from that during the therapy planning.

Here, the image processor 30, the deformation amount evaluator 32, the storage device 34, and the controller 38 which serve as a three-dimensional CT image reproducing unit may be formed by one or more computers. In addition, an analysis process in preparation before the therapy using the CT scan may also be performed using one or more computers. Thus, the relationship between the landmark and the amount of deformation, determined based on the analysis result of the image obtained by the CT scan, and a processing program may be stored in the storage device 34, and the one or more computers may execute the program to produce and reproduce a corresponding three-dimensional CT image based on the landmark positions which are successively detected, and to control the irradiation of the therapeutic radiation based on the obtained three-dimensional CT image.

[Preparation Before Therapy]

Three-dimensional CT images of the patient before the therapy; that is, a plurality of three-dimensional CT images taken with elapse of time, are obtained. For example, for sites which change with respiration such as the lung, the three-dimensional CT images of various phases with the elapse of time are obtained for one period of the respiration. In the present embodiment, 10 sets of three-dimensional CT images are obtained, in which one period of the respiration is divided into 10 phases. The CT images may be obtained with a normal CT scan apparatus.

With a three-dimensional CT image of exhalation as a reference, for each of the three-dimensional CT images of the other phases, (i) an amount of deformation caused in the body, (ii) an amount of displacement of the in-body marker position, and (iii) an amount of change of the body surface shape are evaluated. In other words, based on the measured values of (ii) and (iii), a relationship (function) for evaluating (i) is optimized. A model of the function may be arbitrary, and may be, for example, a linear function. In the present embodiment, the linear function is employed.

[Optimization of Function]

First, with one image among the 10 sets of CT images as a reference image, differences of the other 9 CT images from the reference image are evaluated. For example, the CT image of the exhalation phase is set as reference volume data V0, and 9 three-dimensional deformation fields $D(x,y,z)p$ are calculated through deformable image registration with the CT images of the other respiration phases. Here, p=0 represents the exhalation phase, and p=1~9 represent other phases. Deformation in an x direction is expressed as $Dx(x,y,z)$, deformation in a y direction is expressed as $Dy(x,y,z)$, and deformation in a z direction is expressed as $Dz(x,y,z)$.

Then, an estimation parameter Tp of a position change having a high correlation with $D(x,y,z)p$ is evaluated. For example, a landmark position Mp in each respiration phase CT is calculated, and a landmark position displacement from the landmark position in the reference CT image is evaluated as the estimation parameter Tp (=Mp−Mp(reference)).

Based on the estimation parameter T (vector), a parameter of a function f(T) is determined for evaluating $D(x,y,z)p$ caused in the body.

For example, for each of x, y, and z directions, a deformation model is created for estimating a deformation field $D(x,y,z)$ to be evaluated, using the parameter T (landmark position displacement).

$$Di(x,y,z)=\alpha(x,y,z)Ti+\beta(x,y,z)$$

Here, the parameter i is x, y, or z.

With this process, for each CT image, when the deformation parameter Tp from the landmark position in the reference CT image is determined, the amount of movement of each section in each CT image may be estimated accordingly. For example, with each CT image as voxel data, a three-dimensional CT image may be produced according to the movement vector of the marker.

The landmark may be the in-body marker which is a metal marker or the like embedded in the body, or may alternatively be the patient's diaphragm, a branching part of the patient's lung, or the like.

[Example Calculation]

Figure 2:
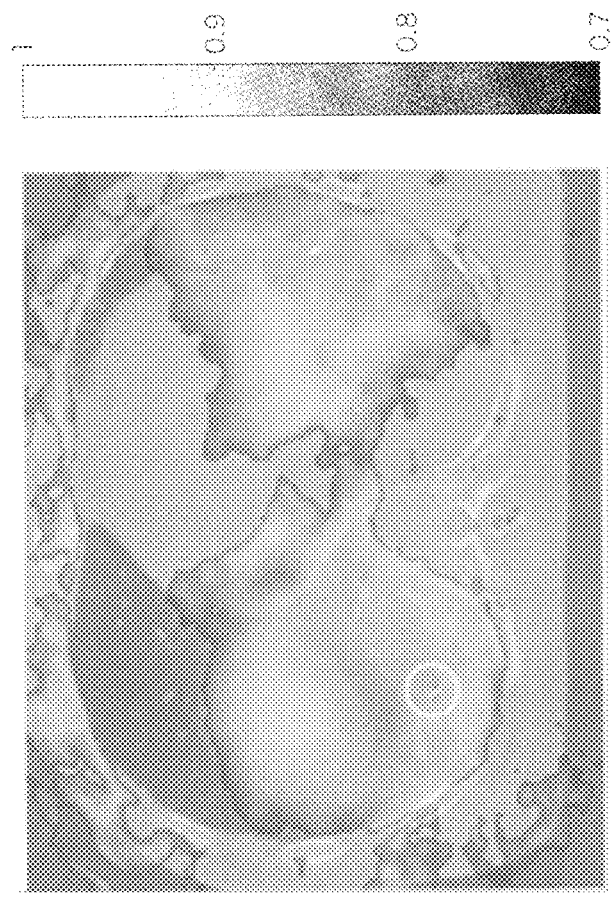
FIG. 2 shows a CT image in an axial plane showing, with brightness, correlation between a marker displacement and deformation in an SI direction.
Figure 3:
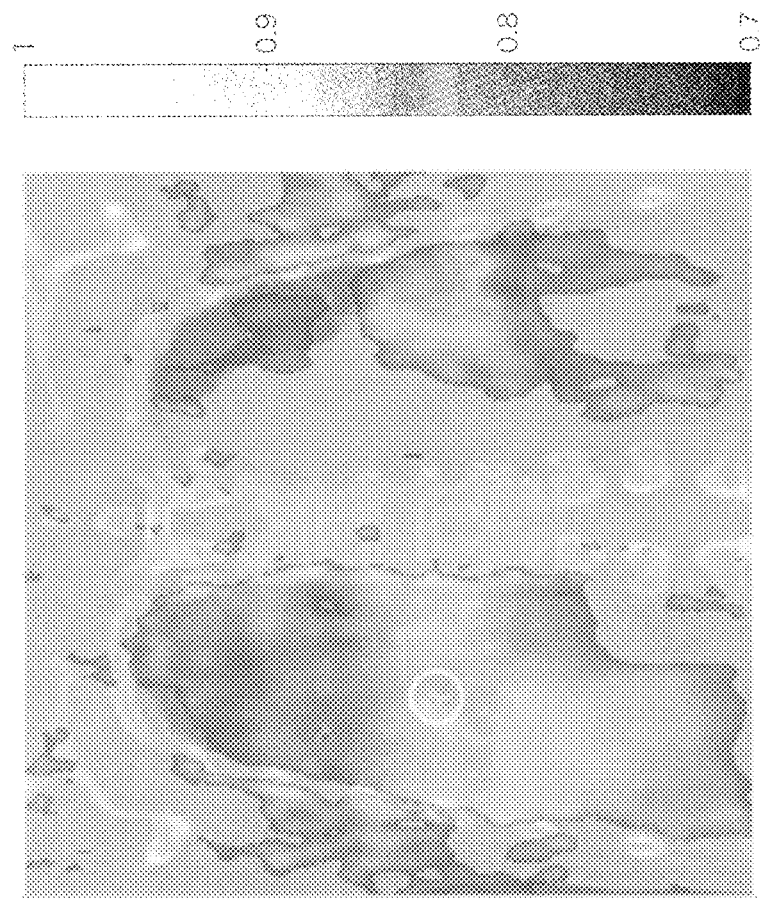
FIG. 3 shows a CT image in a coronal plane showing, with brightness, correlation between a marker displacement and deformation in an SI direction.
Figure 4:
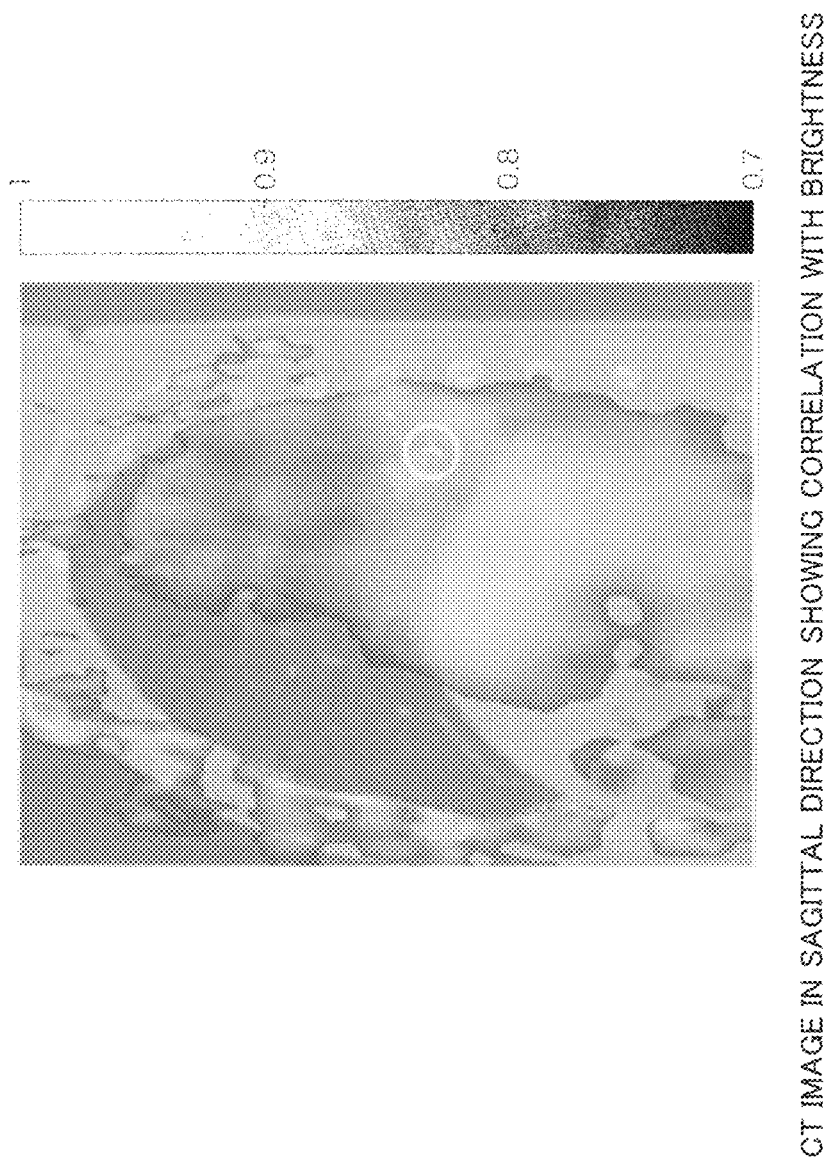
FIG. 4 shows a CT image in a sagittal plane showing, with brightness, correlation between a marker displacement and deformation in an SI direction.

FIGS. 2 to 4 show correlation between the landmark (here, a marker) displacement and an amount of movement of each voxel (in a head-to-foot (SI) direction) for CT images in three directions. FIG. 2 shows an image in axial plane of the body, FIG. 3 shows an image in coronal plane of the body, and FIG. 4 shows an image in sagittal plane of the body. A portion having a high correlation is shown brightly in an island-shape portion in the image. In these figures, a circle shows the marker position. Thus, it can be understood that the correlation is high around the marker.

Figure 5:
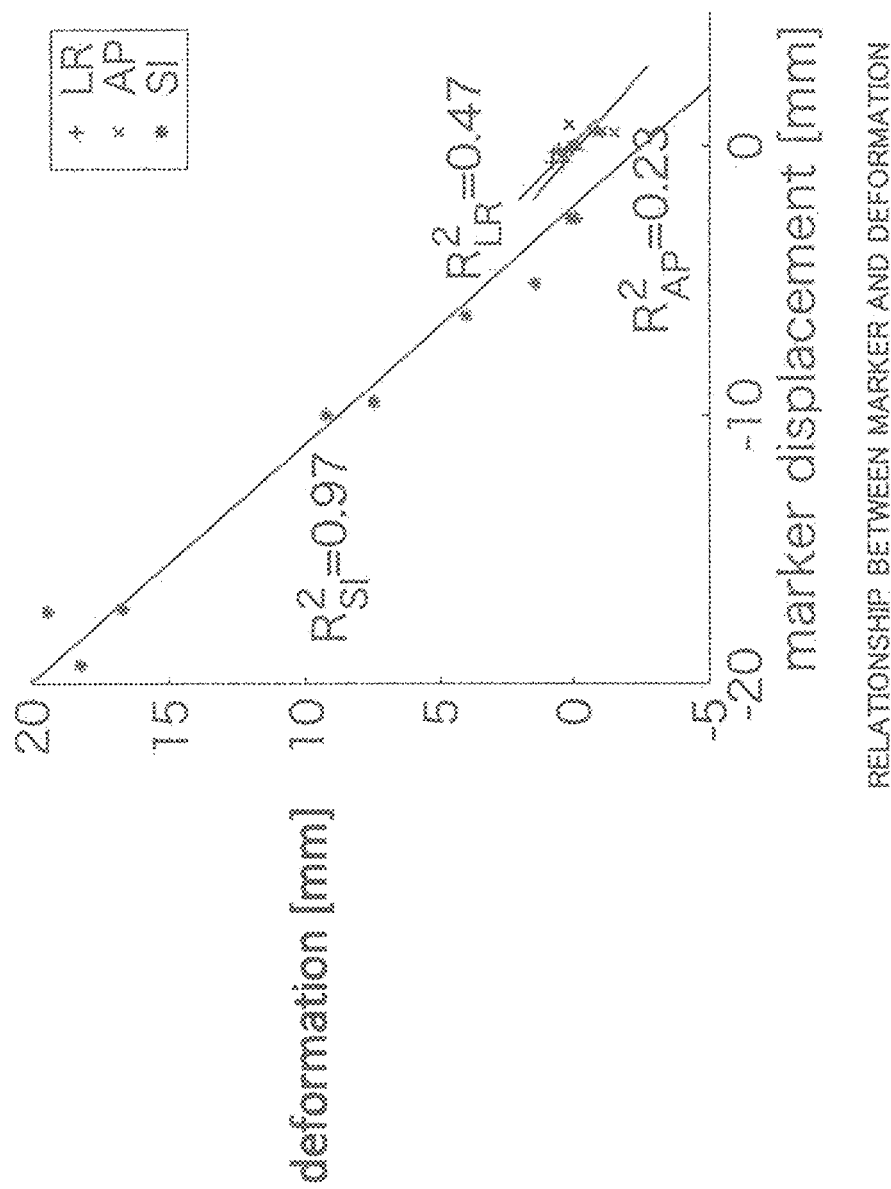
FIG. 5 is a graph showing a relationship between a marker displacement and deformation.

FIG. 5 shows a relationship between the displacement of the marker and the amount of movement of the voxel at a position distanced from the marker by 30 mm. Thus, it can be understood that the movement in the head-to-foot direction (SI direction) has a very high correlation with the displacement of the marker. The correlation is lower for the other two directions, but because the absolute amount of movement is small, the influence on the position precision is low.

Figure 6:
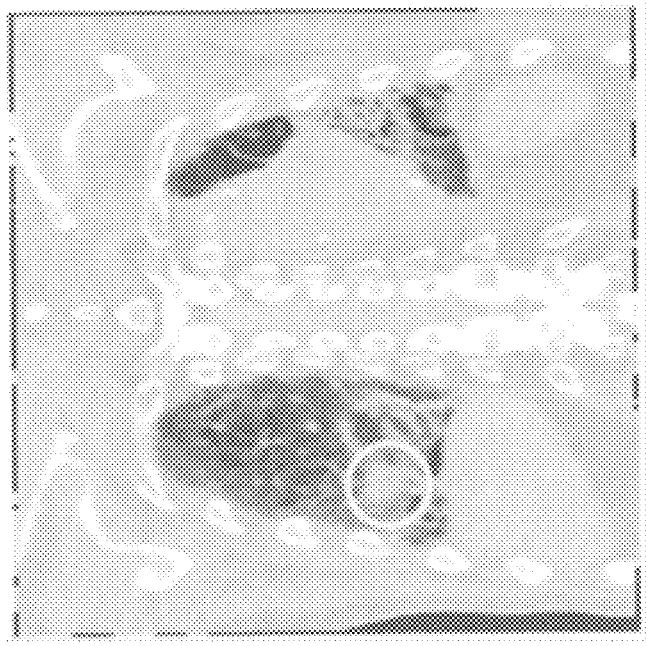
FIG. 6 shows a CT image in a coronal plane in an exhalation phase.
Figure 7:
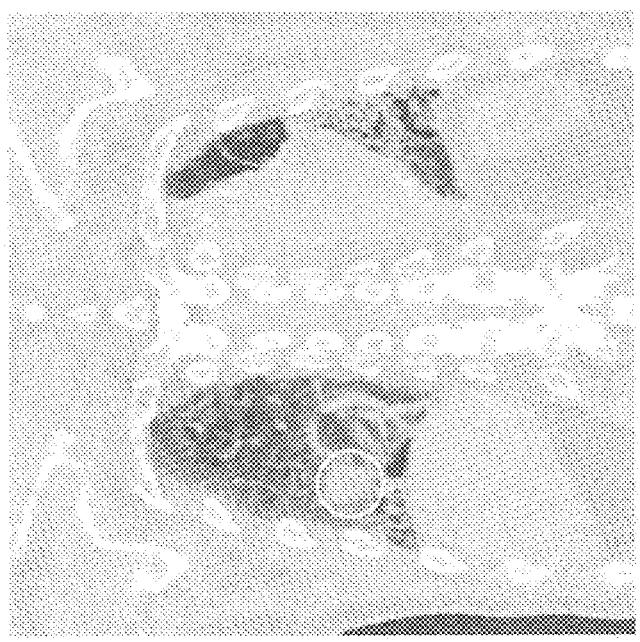
FIG. 7 shows a CT image in a coronal plane in an inspiration phase.
Figure 8:
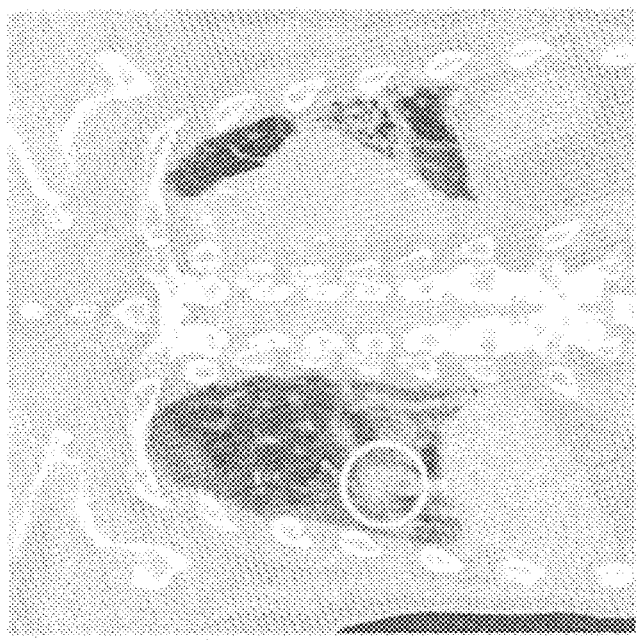
FIG. 8 is a synthesized image in a coronal plane of an inspiration phase determined through a calculation.
Figure 9:
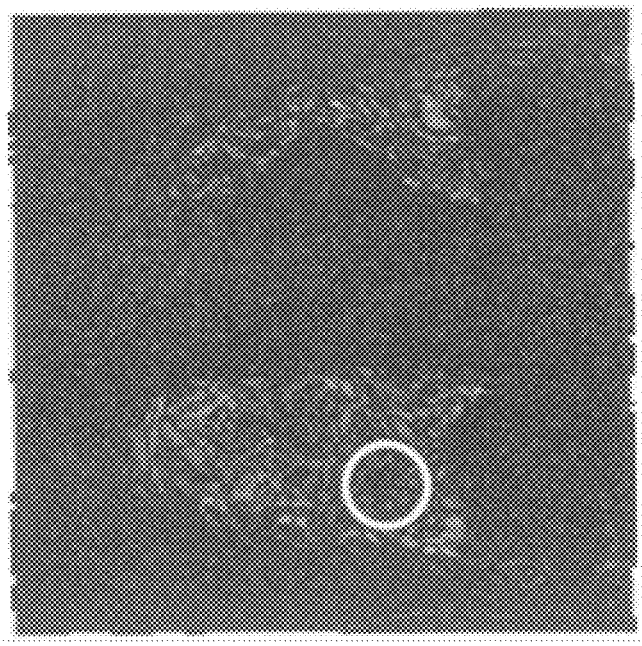
FIG. 9 shows an image showing a difference between the CT image of FIG. 7 and the CT image of FIG. 8.

FIG. 6 shows a coronal image (CT image) in the exhalation phase, and FIG. 7 shows a coronal image (CT image) in the inspiration phase. FIG. 8 shows a coronal image (synthesized image) of an estimated inspiration phase, calculated based on the mount of displacement of the marker in the inspiration phase (FIG. 7), based on the coronal image in the exhalation phase. Thus, it can be understood that the synthesized image of the inspiration phase which is estimated and shown in FIG. 8 is very close to that of the inspiration phase of FIG. 7. FIG. 9 shows a difference between the images of FIGS. 7 and 8. A portion of high brightness in FIG. 9 shows a portion with a large difference. In the figures, it can be understood that there is almost no difference for a region around the marker, shown by a white circle.

[Others]

In the above-described example configuration, the CT image is reproduced based on the position of the in-body marker. In this process, precision of the reproduced CT image can be improved by associating with these data other data such as the body surface position. For example, a relationship between a change of the body surface position around the marker and a change of voxels of each section (for example, a linear correlation relationship) may be determined. During the therapy, the body surface position may be detected in addition to the marker position, and each voxel position obtained based on the marker displacement may be corrected using the position of each voxel calculated based on the body surface position (or a statistical quantity thereof). For example, the position may be calculated through a weighted averaging of these voxel positions.

As described, according to the present embodiment, the position of the marker 14 is detected based on the images obtained in real time by the X-ray cameras 20, 20, and the three-dimensional CT image at each point in time is reproduced in real time based on the detected marker position.

Thus, the irradiation of the therapeutic radiation beam from the beam irradiation apparatus 40 can be controlled while referring to the three-dimensional CT images which are routinely obtained.

With such a configuration, the therapeutic radiation beam can be reliably irradiated tracing a diseased part which moves greatly, or to a particular position of the diseased part, resulting in suppression of wasteful irradiation of the radiation.

By evaluating an in-body structure based on the three-dimensional position of the marker embedded in the body of the patient and/or the landmark position which can be obtained in real time such as the body surface shape information, a consistency between the evaluated in-body structure and the CT image at the time of the therapy planning can be evaluated, and, consequently, the therapeutic radiation can be controlled in real time during the therapy.

REFERENCE SIGNS LIST

10 THERAPEUTIC TABLE; 12 PATIENT; 14 MARKER; 20 X-RAY CAMERA; 22 X-RAY IRRADIATION APPARATUS; 24 X-RAY CAMERA INTERFACE; 26 OPTICAL CAMERA; 28 OPTICAL CAMERA INTERFACE; 30 IMAGE PROCESSOR; 32 DEFORMATION AMOUNT EVALUATOR; 34 STORAGE DEVICE; 36 DISPLAY; 38 CONTROLLER; 40 BEAM IRRADIATION APPARATUS.

The invention claimed is:

1. A radiotherapy apparatus comprising: a detector unit that detects a landmark present in an irradiation target, the detector unit including at least two X-ray irradiation sources for outputting X-ray beams, the detector unit including at least two X-ray cameras for detecting the X-ray beams; a storage communicatively coupled with the detector unit to receive a position of the landmark, the storage storing a relationship between a displacement from the position of the landmark in a reference image, which is a one three-dimensional CT image among a plurality of three-dimensional CT images of the irradiation target including the landmark, taken with elapse of time, and which are obtained in advance during therapy planning, to a position of the landmark in another three-dimensional CT image, and deformation of each site in the other CT image; and a deformation amount evaluator communicatively coupled with the storage to receive the relationship, the deformation amount evaluator being configured to estimate deformation of each site by referring to the relationship and according to the position of the landmark detected by the detector unit during a therapy in which a therapeutic radiation is irradiated onto the irradiation target, and that reproduces an estimated three-dimensional CT image.

2. The radiotherapy apparatus according to claim 1, further comprising:
a controller communicatively coupled with the deformation amount evaluator, the controller being configured to control irradiation of the therapeutic radiation based on the reproduced three-dimensional CT image.

3. The radiotherapy apparatus according to claim 2, wherein the control unit compares the reproduced three-dimensional CT image and a three-dimensional CT image which is obtained in advance during the therapy planning, and suspends the irradiation of the therapeutic radiation when a difference between the three-dimensional CT images is greater than or equal to a predetermined level.

4. The radiotherapy apparatus according to claim 1, wherein the landmark includes a metal marker, and the detector unit includes an X-ray camera which detects the metal marker.

5. The radiotherapy apparatus according to claim 1, wherein the landmark includes a surface position of the irradiation target, and the detector unit includes a surface detection apparatus which detects the surface position, the surface detection apparatus including at least one optical camera.

6. A radiotherapy method in which a therapeutic radiation is irradiated onto an irradiation target, the method comprising:
during therapy planning, producing a plurality of three-dimensional CT images of the irradiation target including a landmark present in the irradiation target, taken with elapse of time, analyzing a relationship between a displacement from a position of the landmark in a reference image, which is one three-dimensional CT image among the plurality of three-dimensional CT image which are obtained, to a position of the landmark in another three-dimensional CT image, and deformation of each site in the other CT image, and storing the relationship which is obtained; and
during therapy in which a radiation is irradiated onto the irradiation target, detecting the position of the landmark, estimating deformation of each site by referring to the relationship and according to the detected position of the landmark, and obtaining a three-dimensional CT image.

7. The radiotherapy method according to claim 6, wherein the irradiation of the therapeutic radiation is controlled based on the three-dimensional CT image which is obtained.

* * * * *